US009119810B2

(12) United States Patent
Montelione et al.

(10) Patent No.: US 9,119,810 B2

(45) Date of Patent: Sep. 1, 2015

(54) COMPOSITIONS AND VACCINES AGAINST INFLUENZA A AND INFLUENZA B INFECTIONS

(75) Inventors: Gaetano T. Montelione, Highland Park, NJ (US); Robert M. Krug, Austin, TX (US); Yin Cuifeng, Princeton, NJ (US); Ma Lichung, Plainsboro, NJ (US)

(73) Assignees: Rutgers, The State University of New Jersey, New Brunswick, NJ (US); Robert M. Krug, Austin, TX (US)

( * ) Notice: Subject to any disclaimer, the term of this patent is extended or adjusted under 35 U.S.C. 154(b) by 659 days.

(21) Appl. No.: 12/094,114

(22) PCT Filed: Nov. 17, 2006

(86) PCT No.: PCT/US2006/044930

§ 371 (c)(1),
(2), (4) Date: Oct. 27, 2008

(87) PCT Pub. No.: WO2007/061969

PCT Pub. Date: May 31, 2007

(65) Prior Publication Data

US 2010/0291128 A1 Nov. 18, 2010

Related U.S. Application Data

(60) Provisional application No. 60/737,742, filed on Nov. 18, 2005.

(51) Int. Cl.
*A61K 39/145* (2006.01)
*A61K 39/00* (2006.01)

(52) U.S. Cl.
CPC ............... *A61K 39/145* (2013.01); *A61K 39/00* (2013.01); *A61K 2039/5254* (2013.01); *A61K 2039/53* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS 5,166,057 A * 11/1992 Palese et al. ................. 435/69.1

FOREIGN PATENT DOCUMENTS

| | | | |
|---|---|---|---|
| EP | 0366239 A1 * | 5/1990 |
| WO | WO 9315763 A1 * | 8/1993 |
| WO | 2004043404 | 5/2004 |
| WO | WO 2005095974 A1 * | 10/2005 |

OTHER PUBLICATIONS

Donelan et al (Journal of Virology 77:13257-13266, 2003).*
Ferko et al (Journal of Virology 78:13037-13045, 2004).*
Donelan (Journal of Virology 78:11574-11582, 2004).*
Tomoda et al (Vaccine 13:185-190, 1995).*
Li et al (Journal of Infectious Diseases 179:1132-138, 1999).*
Wang et al (RNA 5:195-205, 1999; in IDS).*

(Continued)

*Primary Examiner* — Zachariah Lucas
*Assistant Examiner* — M. Franco Salvoza
(74) *Attorney, Agent, or Firm* — Fox Rothschild LLP; Gerard P. Norton; Jainming Jimmy Hao

(57) ABSTRACT

Novel models of interactions of the Nonstructural Protein of influenza A and influenza B viruses (NS1A and NS1B, respectively) with dsRNA are presented. On the basis of the models, novel recombinant viruses and vaccines against influenza A and influenza B viruses are provided.

16 Claims, 2 Drawing Sheets

(56) References Cited

OTHER PUBLICATIONS

Genbank accession AAC35578, Dec. 1, 2008.*

Genbank accession AAO52929, Mar. 15, 2003.*

Genbank accession CAD23745, Apr. 15, 2005.*

Genbank accession AAA55185.1, Sequence 6, May 2, 1990.*

Genbank accession AAA55186.1, Sequence 8, May 2, 1990.*

Chien et al., "Biophysical Characterization of the Complex between Double-Stranded RNA and N-Terminal Domain of the NS1 Protein from Influenza A Virus: Evidence for a Novel RNA-Binding Mode," Biochemistry (2004): vol. 43; pp. 1950-1962.

Qian et al., "Two Functional Domains of the Influenza Virus NS1 Protein Are Required for Regulation of Nuclear Export of mRNA," Journal of Virology (Apr. 1994): vol. 68, No. 4; pp. 2433-2441.

Qian et al., "An amino-terminal polypeptide fragment of the influenza virus NS1 protein possesses specific RNA-binding activity and largely helical backbone structure," RNA (1995): vol. 1; pp. 948-956.

Chien et al., "A novel RNA-binding motif in influenza A virus nonstructural protein 1," Nature Structural Biology (Nov. 1997): vol. 4, No. 11; pp. 891-895.

Liu et al., "Crystal structure of the unique RNA-binding domain of the influenza virus NS1 protein," Nature Structural Biology (Nov. 1997): vol. 4, No. 11; pp. 896-899.

Wang et al., "RNA binding by the novel helical domain of the influenza virus NS1 protein requires its dimer structure and a small number of specific basic amino acids," RNA (1999): vol. 5; pp. 195-205.

* cited by examiner

Fig. 1. Stereo-images of NS1A(1-73) binding to dsRNA
Conserved surface residues of dsRNA-binding epitope are shaded
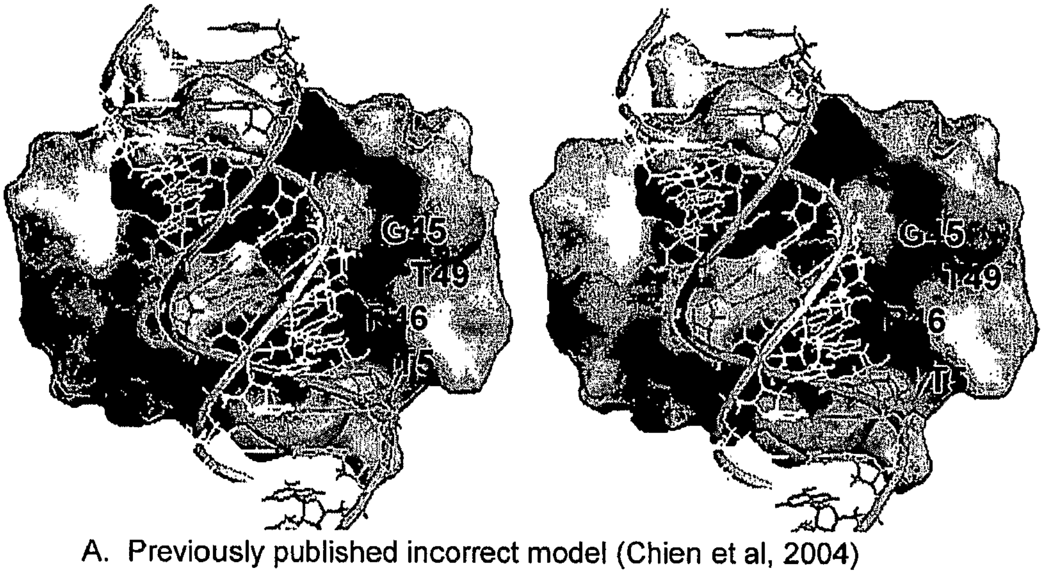
A. Previously published incorrect model (Chien et al, 2004)
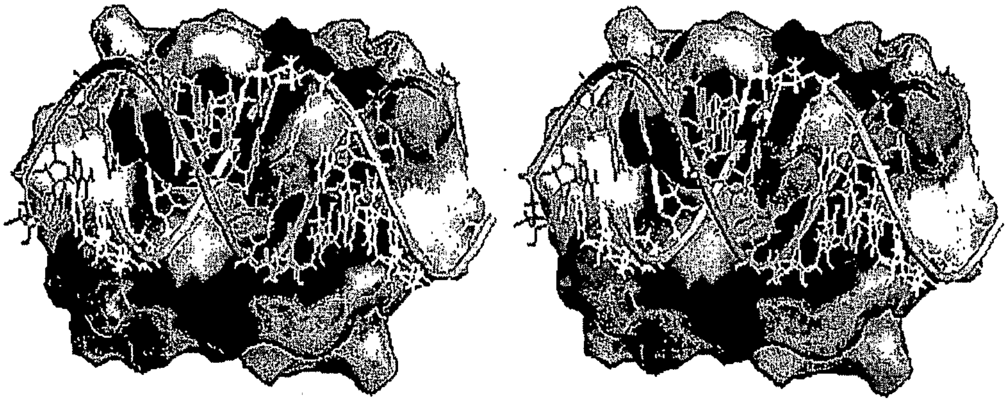
B. Major-groove binding model
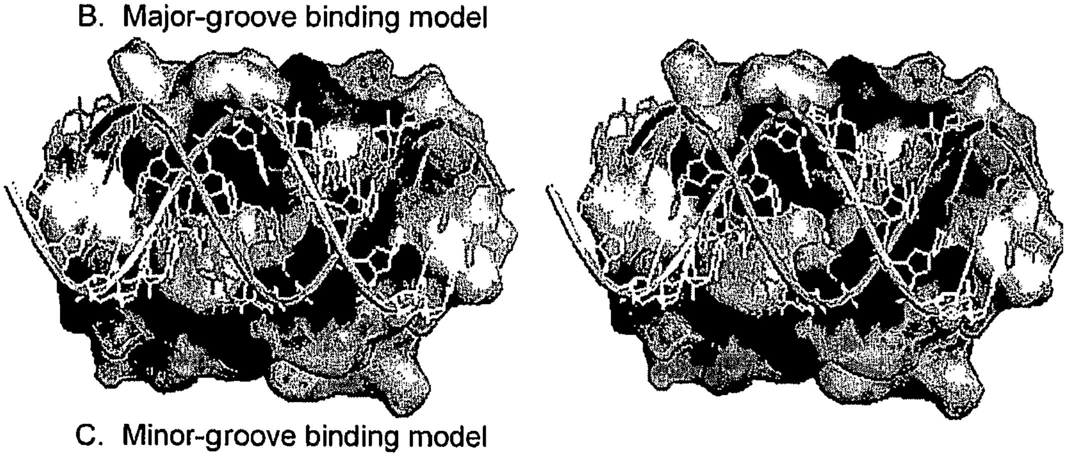
C. Minor-groove binding model Fig. 2 Stereo-image of NS1B(1-103) binding to dsRNA
Conserved surface residues of dsRNA-binding epitope are colored
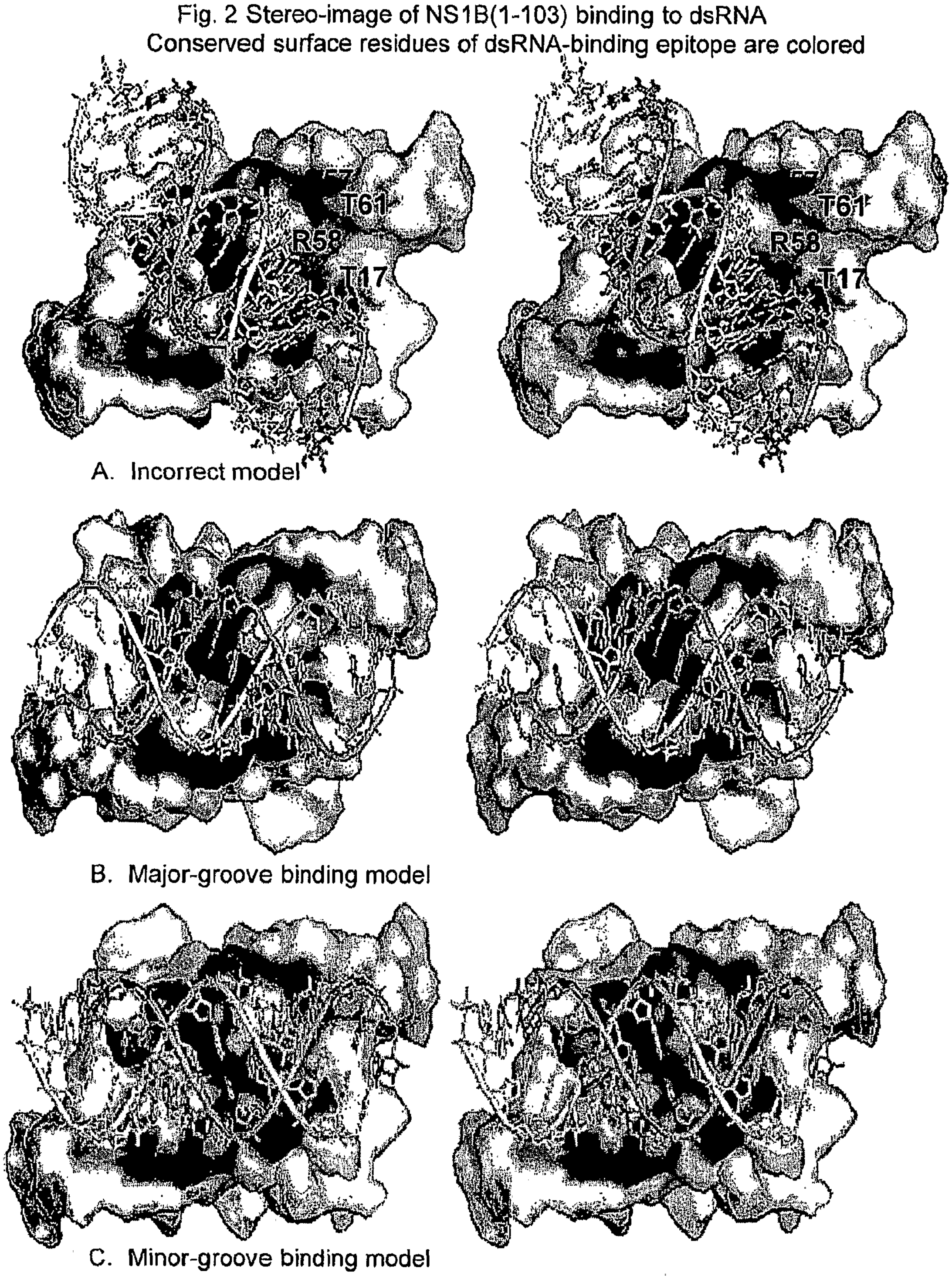

SEQUENCE LISTING

```
<160> NUMBER OF SEQ ID NOS: 25

<210> SEQ ID NO 1
<211> LENGTH: 73
<212> TYPE: PRT
<213> ORGANISM: Influenza A virus

<400> SEQUENCE: 1

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
```

-continued

```
        35                  40                  45

Thr Leu Gly Leu Asp Ile Glu Thr Ala Thr Arg Ala Gly Lys Gln Ile
     50                  55                  60

Val Glu Arg Ile Leu Lys Glu Glu Ser
 65                  70


<210> SEQ ID NO 2
<211> LENGTH: 103
<212> TYPE: PRT
<213> ORGANISM: Influenza B virus

<400> SEQUENCE: 2

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Phe Ser Trp Gln Arg Ala Leu Asp Tyr Pro Gly Gln Asp Arg Leu
        35                  40                  45

His Arg Leu Lys Arg Lys Leu Glu Ser Arg Ile Lys Thr His Asn Lys
     50                  55                  60

Ser Glu Pro Glu Asn Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr
            100


<210> SEQ ID NO 3
<211> LENGTH: 230
<212> TYPE: PRT
<213> ORGANISM: Influenza A virus

<400> SEQUENCE: 3

Met Asp Pro Asn Thr Val Ser Ser Phe Gln Val Asp Cys Phe Leu Trp
  1               5                  10                  15

His Val Arg Lys Arg Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
     50                  55                  60

Val Glu Arg Ile Leu Lys Glu Glu Ser Asp Glu Ala Leu Lys Met Thr
 65                  70                  75                  80

Met Ala Ser Val Pro Ala Ser Arg Tyr Leu Thr Asp Met Thr Leu Glu
                 85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
```

```
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230


<210> SEQ ID NO 4
<211> LENGTH: 230
<212> TYPE: PRT
<213> ORGANISM: Influenza A virus

<400> SEQUENCE: 4

Met Asp Ser Asn Thr Ile Thr Ser Phe Gln Val Asp Cys Tyr Leu Trp
  1               5                  10                  15

His Ile Arg Lys Leu Leu Ser Met Ser Asp Met Cys Asp Ala Pro Phe
            20                  25                  30

Asp Asp Arg Leu Arg Arg Asp Gln Lys Ala Leu Lys Gly Arg Gly Ser
        35                  40                  45

Thr Leu Gly Leu Asp Leu Arg Val Ala Thr Met Glu Gly Lys Lys Ile
     50                  55                  60

Val Glu Asp Ile Leu Lys Ser Glu Thr Asn Glu Asn Leu Lys Ile Ala
 65                  70                  75                  80

Ile Ala Ser Ser Pro Ala Pro Arg Tyr Val Thr Asp Met Ser Ile Glu
                 85                  90                  95

Glu Met Ser Arg Glu Trp Tyr Met Leu Met Pro Arg Gln Lys Ile Thr
            100                 105                 110

Gly Gly Leu Met Val Lys Met Asp Gln Ala Ile Met Asp Lys Arg Ile
        115                 120                 125

Ile Leu Lys Ala Asn Phe Ser Val Leu Phe Asp Gln Leu Glu Thr Leu
    130                 135                 140

Val Ser Leu Arg Ala Phe Thr Glu Ser Gly Ala Ile Val Ala Glu Ile
145                 150                 155                 160

Ser Pro Ile Pro Ser Val Pro Gly His Ser Thr Glu Asp Val Lys Asn
                165                 170                 175

Ala Ile Gly Ile Leu Ile Gly Gly Leu Glu Trp Asn Asp Asn Ser Ile
            180                 185                 190

Arg Ala Ser Glu Asn Ile Gln Arg Phe Ala Trp Gly Ile Arg Asp Glu
        195                 200                 205

Asn Gly Gly Pro Ser Leu Pro Pro Lys Gln Lys Arg Tyr Met Ala Lys
    210                 215                 220

Arg Val Glu Ser Glu Val
225                 230


<210> SEQ ID NO 5
<211> LENGTH: 173
<212> TYPE: PRT
<213> ORGANISM: Influenza A virus

<400> SEQUENCE: 5

Glu Leu Gly Asp Ala Pro Phe Leu Asp Arg Leu Arg Arg Asp Gln Lys
  1               5                  10                  15

Ser Leu Lys Gly Arg Gly Ser Thr Leu Gly Leu Asn Ile Glu Thr Ala
            20                  25                  30

Thr Cys Val Gly Lys Gln Ile Val Glu Arg Ile Leu Lys Glu Glu Ser
```

```
        35                  40                  45

Asp Glu Ala Phe Lys Met Thr Met Ala Ser Ala Leu Ala Ser Arg Tyr
     50                  55                  60

Leu Thr Asp Met Thr Ile Glu Glu Met Ser Arg Asp Trp Phe Met Leu
 65                  70                  75                  80

Met Pro Lys Gln Lys Val Ala Gly Pro Leu Cys Val Arg Met Asp Gln
                 85                  90                  95

Ala Ile Met Asp Lys Asn Ile Ile Leu Lys Ala Asn Phe Ser Val Ile
            100                 105                 110

Phe Asp Arg Leu Glu Thr Leu Thr Leu Leu Arg Ala Phe Thr Glu Glu
        115                 120                 125

Gly Ala Ile Val Gly Glu Ile Ser Pro Leu Pro Ser Leu Pro Gly His
    130                 135                 140

Thr Asn Glu Asp Val Lys Asn Ala Ile Gly Val Leu Ile Gly Gly Leu
145                 150                 155                 160

Glu Trp Asn Asp Asn Thr Val Arg Val Ser Glu Thr Leu
                165                 170


<210> SEQ ID NO 6
<211> LENGTH: 230
<212> TYPE: PRT
<213> ORGANISM: Influenza A virus

<400> SEQUENCE: 6

Met Asp Ser Asn Thr Val Ser Ser Phe Gln Val Asp Cys Phe Leu Trp
  1               5                  10                  15

His Val Arg Lys Arg Phe Ala Asp Gln Glu Met Gly Asp Ala Pro Phe
            20                  25                  30

Leu Asp Arg Leu Arg Arg Asp Gln Lys Ser Leu Gly Gly Arg Gly Ser
        35                  40                  45

Thr Leu Gly Leu Asp Ile Glu Thr Ala Thr Arg Ala Gly Lys Gln Ile
     50                  55                  60

Val Glu Pro Ile Leu Glu Glu Glu Ser Asp Glu Ala Leu Lys Met Thr
 65                  70                  75                  80

Ile Ala Ser Ala Pro Val Ser Arg Tyr Leu Pro Asp Met Thr Leu Glu
                 85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Lys Asn Ile
        115                 120                 125

Thr Leu Lys Ala Asn Phe Ser Ile Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Val Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Asp Ser Glu Thr Leu Gln Arg Phe Ala Trp Arg Ser Ser Asn Glu
        195                 200                 205

Asp Arg Arg Pro Pro Leu Pro Pro Lys Gln Lys Arg Lys Met Ala Arg
    210                 215                 220

Thr Ile Glu Ser Glu Val
225                 230
```

<210> SEQ ID NO 7
<211> LENGTH: 230
<212> TYPE: PRT
<213> ORGANISM: Influenza A virus

<400> SEQUENCE: 7

```
Met Asp Ser Asn Thr Val Ser Ser Phe Gln Val Asp Cys Phe Leu Trp
  1               5                  10                  15

His Val Arg Lys Arg Phe Ala Asp Gln Glu Arg Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asp Ile Glu Thr Ala Thr Cys Ala Gly Lys Gln Ile
     50                  55                  60

Val Glu Arg Ile Leu Lys Glu Glu Ser Asp Glu Ala Leu Lys Met Thr
 65                  70                  75                  80

Ile Ala Ser Val Pro Ala Ser Arg Tyr Leu Thr Asp Met Thr Leu Glu
                 85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Phe Pro Pro Lys Gln Lys Arg Lys Met Ala Arg
    210                 215                 220

Thr Ile Glu Ser Glu Val
225                 230
```

<210> SEQ ID NO 8
<211> LENGTH: 230
<212> TYPE: PRT
<213> ORGANISM: Influenza A virus

<400> SEQUENCE: 8

```
Met Asp Ser Asn Thr Val Ser Ser Phe Gln Val Asp Cys Phe Leu Trp
  1               5                  10                  15

His Val Arg Lys Arg Phe Ala Asp Gln Lys Leu Gly Asp Ala Pro Phe
             20                  25                  30

Leu Asp Arg Leu Arg Arg Asp Gln Lys Ser Leu Arg Gly Arg Ala Ser
         35                  40                  45

Thr Leu Gly Leu Asp Ile Glu Thr Ala Thr Arg Ala Gly Lys Gln Ile
     50                  55                  60

Val Glu Arg Ile Leu Glu Glu Glu Ser Asn Glu Ala Leu Lys Met Thr
 65                  70                  75                  80

Ile Ala Ser Val Pro Ala Ser Arg Tyr Leu Thr Asp Met Thr Leu Glu
                 85                  90                  95
```

-continued

```
Glu Met Ser Arg Asp Trp Phe Met Leu Met Pro Lys Gln Lys Val Ala
            100                 105                 110

Gly Ser Leu Cys Ile Arg Met Asp Gln Ala Ile Met Glu Lys Ser Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu His Ser Leu Pro Gly His Thr Asp Glu Asp Val Lys Asn
                165                 170                 175

Ala Val Gly Val Leu Ile Gly Gly Leu Glu Trp Asn Gly Asn Thr Val
            180                 185                 190

Arg Val Ser Glu Asn Leu Gln Arg Phe Ala Trp Arg Ser Arg Asn Glu
        195                 200                 205

Asn Glu Arg Pro Ser Leu Pro Pro Lys Gln Lys Arg Glu Val Ala Gly
    210                 215                 220

Thr Ile Arg Ser Glu Val
225                 230


<210> SEQ ID NO 9
<211> LENGTH: 227
<212> TYPE: PRT
<213> ORGANISM: Influenza A virus

<400> SEQUENCE: 9

Asn Thr Val Ser Ser Phe Gln Val Asp Cys Phe Leu Trp His Val Arg
  1               5                  10                  15

Lys Arg Phe Ala Asp Gln Glu Leu Gly Asp Ala Pro Phe Leu Asp Arg
             20                  25                  30

Leu Arg Arg Asp Gln Lys Ser Leu Arg Gly Arg Gly Ser Thr Leu Gly
         35                  40                  45

Leu Asp Ile Glu Thr Ala Thr Arg Ala Gly Lys Gln Ile Val Glu Arg
     50                  55                  60

Ile Leu Val Glu Glu Ser Asp Glu Ala Leu Lys Met Thr Ile Val Ser
 65                  70                  75                  80

Met Pro Ala Ser Arg Tyr Leu Thr Asp Met Thr Leu Glu Glu Met Ser
                 85                  90                  95

Arg Asp Trp Phe Met Leu Met Pro Lys Gln Lys Val Ala Gly Ser Leu
            100                 105                 110

Cys Ile Arg Met Asp Gln Ala Ile Met Asp Lys Asn Ile Ile Leu Lys
        115                 120                 125

Ala Asn Phe Ser Val Ile Ser Asp Arg Leu Glu Thr Leu Ile Leu Leu
    130                 135                 140

Arg Ala Phe Thr Glu Glu Gly Ala Ile Val Gly Glu Ile Ser Pro Leu
145                 150                 155                 160

Pro Ser Leu Pro Gly His Thr Asp Glu Asp Val Lys Asn Ala Ile Gly
                165                 170                 175

Asp Leu Ile Gly Gly Leu Glu Trp Asn Asp Asn Thr Val Arg Val Ser
            180                 185                 190

Glu Thr Leu Gln Arg Phe Ala Trp Arg Ser Ser Asn Glu Asp Gly Arg
        195                 200                 205

Pro Leu Leu Pro Pro Lys Gln Lys Arg Lys Met Ala Arg Thr Ile Glu
    210                 215                 220

Ser Glu Val
225
```

<210> SEQ ID NO 10
<211> LENGTH: 217
<212> TYPE: PRT
<213> ORGANISM: Influenza A virus

<400> SEQUENCE: 10

Met Asp Pro Asn Thr Val Ser Ser Phe Gln Val Asp Cys Phe Leu Trp
1 5 10 15

His Val Arg Lys Gln Val Ala Asp Gln Glu Leu Gly Asp Ala Pro Phe
20 25 30

Leu Asp Arg Leu Arg Arg Asp Gln Lys Ser Leu Arg Gly Arg Gly Ser
35 40 45

Thr Leu Gly Leu Asn Ile Glu Thr Ala Thr Arg Val Gly Lys Gln Ile
50 55 60

Val Glu Arg Ile Leu Lys Glu Glu Ser Asp Glu Ala Leu Lys Met Thr
65 70 75 80

Met Ala Ser Ala Pro Ala Ser Arg Tyr Leu Thr Asp Met Thr Ile Glu
85 90 95

Glu Met Ser Arg Asp Trp Phe Met Leu Met Pro Lys Gln Lys Val Ala
100 105 110

Gly Pro Leu Cys Ile Arg Met Asp Gln Ala Ile Met Asp Lys Asn Ile
115 120 125

Ile Leu Lys Ala Asn Phe Ser Val Ile Phe Asp Arg Leu Glu Thr Leu
130 135 140

Ile Leu Leu Arg Ala Phe Thr Glu Ala Gly Ala Ile Val Gly Glu Ile
145 150 155 160

Ser Pro Leu Pro Ser Leu Pro Gly His Thr Asn Glu Asp Val Lys Asn
165 170 175

Ala Ile Gly Val Leu Ile Gly Gly Leu Glu Trp Asn Asp Asn Thr Val
180 185 190

Arg Val Ser Lys Thr Leu Gln Arg Phe Ala Trp Arg Ser Ser Asp Glu
195 200 205

Asn Gly Arg Pro Pro Leu Thr Pro Lys
210 215

<210> SEQ ID NO 11
<211> LENGTH: 227
<212> TYPE: PRT
<213> ORGANISM: Influenza A virus

<400> SEQUENCE: 11

Asn Thr Val Ser Ser Phe Gln Val Asp Cys Phe Leu Trp His Val Leu
1 5 10 15

Lys Arg Phe Ala Asp Gln Glu Leu Gly Asp Ala Pro Phe Leu Asp Arg
20 25 30

Leu Arg Arg Asp Gln Lys Ser Leu Arg Gly Arg Gly Ser Thr Leu Gly
35 40 45

Leu Asp Ile Glu Thr Ala Thr Arg Ala Gly Lys Gln Ile Val Glu Arg
50 55 60

Ile Leu Glu Glu Glu Ser Asp Glu Ala Leu Lys Met Asn Ile Ala Ser
65 70 75 80

Val Pro Ala Ser Arg Tyr Leu Thr Asp Met Thr Leu Glu Glu Met Ser
85 90 95

Arg Asp Trp Phe Met Leu Met Pro Lys Gln Lys Val Ala Gly Ser Leu
100 105 110

```
Cys Ile Arg Met Asp Gln Ala Ile Met Asp Lys Asn Ile Ile Leu Lys
        115                 120                 125

Ala Asn Phe Ser Val Ile Phe Asp Arg Leu Glu Thr Leu Ile Leu Leu
    130                 135                 140

Arg Ala Phe Thr Glu Glu Gly Ala Ile Val Gly Glu Ile Ser Pro Leu
145                 150                 155                 160

Pro Ser Leu Pro Gly His Thr Asp Glu Asp Val Lys Asn Ala Ile Gly
                165                 170                 175

Ile Leu Ile Gly Gly Leu Glu Trp Asn Asp Asn Thr Val Arg Val Ser
            180                 185                 190

Glu Thr Leu Gln Arg Phe Ala Trp Arg Ser Ser Asn Glu Asp Gly Arg
        195                 200                 205

Pro Pro Leu Pro Pro Lys Gln Lys Trp Lys Met Ala Arg Thr Ile Glu
    210                 215                 220

Pro Glu Val
225


<210> SEQ ID NO 12
<211> LENGTH: 227
<212> TYPE: PRT
<213> ORGANISM: Influenza A virus

<400> SEQUENCE: 12

Asn Thr Val Ser Ser Phe Gln Val Asp Cys Phe Leu Trp His Val Arg
  1               5                  10                  15

Lys Arg Phe Ala Asp Leu Glu Leu Gly Asp Ala Pro Phe Leu Asp Arg
            20                  25                  30

Leu Cys Arg Asp Gln Lys Ser Leu Arg Gly Arg Ser Ser Thr Leu Gly
        35                  40                  45

Leu Asp Ile Glu Thr Ala Thr Arg Ala Gly Lys Gln Ile Val Glu Arg
    50                  55                  60

Ile Leu Glu Glu Glu Ser Asp Glu Thr Leu Lys Met Thr Ile Ala Ser
65                  70                  75                  80

Ala Pro Ala Phe Arg Tyr Pro Thr Asp Met Thr Leu Glu Glu Met Ser
                85                  90                  95

Arg Asp Trp Phe Met Leu Met Pro Lys Gln Lys Val Ala Gly Ser Leu
            100                 105                 110

Cys Ile Arg Met Asp Gln Ala Ile Met Asp Lys Asn Ile Ile Leu Lys
        115                 120                 125

Ala Asn Phe Ser Val Ile Phe Asp Arg Leu Glu Thr Leu Ile Leu Leu
    130                 135                 140

Arg Ala Phe Thr Glu Glu Gly Ala Ile Val Gly Glu Ile Ser Pro Leu
145                 150                 155                 160

Pro Ser Leu Pro Gly His Thr Asn Glu Asp Val Lys Asn Ala Ile Gly
                165                 170                 175

Asp Leu Ile Gly Gly Leu Glu Trp Asn Asp Asn Thr Val Arg Val Ser
            180                 185                 190

Glu Thr Leu Gln Arg Phe Ala Trp Arg Ser Ser Asn Glu Gly Gly Arg
        195                 200                 205

Pro Pro Leu Pro Pro Lys Gln Lys Arg Lys Met Ala Arg Thr Ile Glu
    210                 215                 220

Ser Glu Val
225
```

<210> SEQ ID NO 13
<211> LENGTH: 230
<212> TYPE: PRT
<213> ORGANISM: Influenza A virus

<400> SEQUENCE: 13

Met Asp Ser Asn Thr Ile Thr Ser Phe Gln Val Asp Cys Tyr Leu Trp
1 5 10 15

His Ile Arg Lys Leu Leu Ser Met Arg Asp Met Cys Asp Ala Pro Phe
20 25 30

Asp Asp Arg Leu Arg Arg Asp Gln Lys Ala Leu Lys Gly Arg Gly Ser
35 40 45

Thr Leu Gly Leu Asp Leu Arg Val Ala Thr Met Glu Gly Lys Lys Ile
50 55 60

Val Glu Asp Ile Leu Lys Ser Glu Thr Asp Glu Asn Leu Lys Ile Ala
65 70 75 80

Ile Ala Ser Ser Pro Ala Pro Arg Tyr Ile Thr Asp Met Ser Ile Glu
85 90 95

Glu Ile Ser Arg Glu Trp Tyr Met Leu Met Pro Arg Gln Lys Ile Thr
100 105 110

Gly Gly Leu Met Val Lys Met Asp Gln Ala Ile Met Asp Lys Arg Ile
115 120 125

Thr Leu Lys Ala Asn Phe Ser Val Leu Phe Asp Gln Leu Glu Thr Leu
130 135 140

Val Ser Leu Arg Ala Phe Thr Asp Asp Gly Ala Ile Val Ala Glu Ile
145 150 155 160

Ser Pro Ile Pro Ser Met Pro Gly His Ser Thr Glu Asp Val Lys Asn
165 170 175

Ala Ile Gly Ile Leu Ile Gly Gly Leu Glu Trp Asn Asp Asn Ser Ile
180 185 190

Arg Ala Ser Glu Asn Ile Gln Arg Phe Ala Trp Gly Ile Arg Asp Glu
195 200 205

Asn Gly Gly Pro Pro Leu Pro Pro Lys Gln Lys Arg Tyr Met Ala Arg
210 215 220

Arg Val Glu Ser Glu Val
225 230

<210> SEQ ID NO 14
<211> LENGTH: 124
<212> TYPE: PRT
<213> ORGANISM: Influenza A virus

<400> SEQUENCE: 14

Met Asp Ser Asn Thr Ile Thr Ser Phe Gln Val Asp Cys Tyr Leu Trp
1 5 10 15

His Ile Arg Lys Leu Leu Ser Met Arg Asp Met Cys Asp Ala Pro Phe
20 25 30

Asp Asp Arg Leu Arg Arg Asp Gln Lys Ala Leu Lys Gly Arg Gly Ser
35 40 45

Thr Leu Gly Leu Asp Leu Arg Val Ala Thr Met Glu Gly Lys Lys Ile
50 55 60

Val Glu Asp Ile Leu Lys Ser Glu Thr Asp Glu Asn Leu Lys Ile Ala
65 70 75 80

Ile Ala Ser Ser Pro Ala Pro Arg Tyr Ile Thr Asp Met Ser Ile Glu
85 90 95

Glu Ile Ser Arg Glu Trp Tyr Met Leu Met Pro Arg Gln Lys Ile Thr

-continued

```
            100                 105                 110

Gly Gly Leu Met Val Arg Pro Leu Trp Thr Arg Gly
        115                 120


<210> SEQ ID NO 15
<211> LENGTH: 230
<212> TYPE: PRT
<213> ORGANISM: Influenza A virus

<400> SEQUENCE: 15

Met Asp Ser Asn Thr Val Ser Ser Phe Gln Val Asp Cys Phe Leu Trp
  1               5                  10                  15

His Val Arg Lys Arg Phe Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asp Ile Arg Thr Ala Thr Arg Glu Gly Lys His Ile
     50                  55                  60

Val Glu Arg Ile Leu Glu Glu Glu Ser Asp Glu Ala Leu Lys Met Thr
 65                  70                  75                  80

Ile Ala Ser Val Pro Ala Ser Arg Tyr Leu Thr Glu Met Thr Leu Glu
                 85                  90                  95

Glu Met Ser Arg Asp Trp Leu Met Leu Ile Pro Lys Gln Lys Val Thr
            100                 105                 110

Gly Pro Leu Cys Ile Arg Met Asp Gln Ala Val Met Gly Lys Thr Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Val Glu Arg
    210                 215                 220

Thr Ile Glu Pro Glu Val
225                 230


<210> SEQ ID NO 16
<211> LENGTH: 202
<212> TYPE: PRT
<213> ORGANISM: Influenza A virus

<400> SEQUENCE: 16

Met Asp Pro Asn Thr Val Ser Ser Phe Gln Val Asp Cys Phe Leu Trp
  1               5                  10                  15

His Val Arg Lys Arg Val Ala Asp Gln Glu Leu Gly Asp Ala Pro Phe
             20                  25                  30

Leu Asp Arg Leu Arg Arg Asp Gln Lys Ser Leu Lys Gly Arg Gly Ser
         35                  40                  45

Thr Leu Gly Leu Asn Ile Glu Thr Ala Thr Arg Val Gly Lys Gln Ile
     50                  55                  60

Val Glu Arg Ile Leu Lys Glu Glu Ser Asp Glu Ala Leu Lys Met Thr
```

```
 65                  70                  75                  80

Met Ala Ser Ala Pro Ala Ser Arg Tyr Leu Thr Asp Met Thr Ile Glu
                 85                  90                  95

Glu Met Ser Arg Asp Trp Phe Met Leu Met Pro Lys Gln Lys Val Ala
            100                 105                 110

Gly Pro Leu Cys Ile Arg Met Asp Gln Ala Ile Met Asp Lys Ser Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala
        195                 200


<210> SEQ ID NO 17
<211> LENGTH: 281
<212> TYPE: PRT
<213> ORGANISM: Influenza B virus

<400> SEQUENCE: 17

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
            20                  25                  30

Arg Phe Ser Trp Gln Arg Ala Leu Asp Tyr Pro Gly Gln Asp Arg Leu
        35                  40                  45

His Arg Leu Lys Arg Lys Leu Glu Ser Arg Ile Lys Thr His Asn Lys
    50                  55                  60

Ser Glu Pro Glu Asn Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Val Lys Asn Pro Ser Thr Ser Lys
            100                 105                 110

Cys Pro Asn Tyr Asp Trp Thr Asp Tyr Pro Pro Thr Pro Gly Lys Tyr
        115                 120                 125

Leu Asp Asp Ile Glu Glu Glu Pro Glu Asn Val Asp His Pro Ile Glu
    130                 135                 140

Val Val Leu Arg Asp Met Asn Asn Lys Asp Ala Arg Gln Lys Ile Lys
145                 150                 155                 160

Asp Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Asp Lys Ser Leu Ser Thr Leu His Arg
        195                 200                 205

Leu Asn Ala Tyr Asp Gln Asn Gly Gly Leu Val Ala Lys Leu Val Ala
    210                 215                 220

Thr Asp Asp Arg Thr Val Glu Asp Glu Lys Asp Gly His Arg Ile Leu
225                 230                 235                 240
```

-continued

```
Asn Ser Leu Phe Glu Arg Phe Asp Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280
```

<210> SEQ ID NO 18
<211> LENGTH: 281
<212> TYPE: PRT
<213> ORGANISM: Influenza B virus

<400> SEQUENCE: 18

```
Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Leu Ser Trp Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
     50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Met Lys Ser Ser Ser Asn Ser Asn
            100                 105                 110

Cys Pro Lys Tyr Asn Trp Thr Asp Tyr Pro Ser Thr Pro Gly Arg Cys
        115                 120                 125

Leu Asp Asp Ile Glu Glu Glu Pro Glu Asp Val Asp Gly Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280
```

<210> SEQ ID NO 19
<211> LENGTH: 281
<212> TYPE: PRT
<213> ORGANISM: Influenza B virus

<400> SEQUENCE: 19

```
Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Leu Ser Trp Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
     50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asn Pro Ser Ala Gly
                 85                  90                  95

Ile Glu Gly Phe Glu Pro Tyr Cys Met Lys Asn Ser Ser Asn Ser Asn
            100                 105                 110

Cys Pro Asn Cys Asn Trp Thr Asp Tyr Pro Pro Thr Ser Gly Lys Cys
        115                 120                 125

Leu Asp Asp Ile Glu Glu Glu Pro Glu Asn Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Phe Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 20
<211> LENGTH: 281
<212> TYPE: PRT
<213> ORGANISM: Influenza B virus

<400> SEQUENCE: 20

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Leu Ser Ser Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
     50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asn Pro Ser Ala Gly
                 85                  90                  95
```

```
Ile Glu Gly Phe Glu Pro Tyr Cys Met Lys Asn Ser Ser Asn Ser Asn
            100                 105                 110

Cys Pro Asn Cys Asn Trp Thr Asp Tyr Pro Pro Thr Pro Gly Lys Cys
        115                 120                 125

Leu Asp Asp Ile Glu Glu Glu Pro Glu Asn Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Phe Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 21
<211> LENGTH: 281
<212> TYPE: PRT
<213> ORGANISM: Influenza B virus

<400> SEQUENCE: 21

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Phe Ser Trp Gln Arg Ala Leu Asp Tyr Pro Gly Gln Asp Arg Leu
         35                  40                  45

His Arg Leu Lys Arg Lys Leu Glu Ser Arg Ile Lys Thr His Asn Lys
     50                  55                  60

Ser Glu Pro Glu Asn Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Val Lys Asn Pro Ser Thr Ser Lys
            100                 105                 110

Cys Pro Asn Tyr Asp Trp Thr Asp Tyr Pro Pro Thr Pro Gly Lys Tyr
        115                 120                 125

Leu Asp Asp Ile Glu Glu Glu Pro Glu Asn Val Asp His Pro Ile Glu
    130                 135                 140

Val Val Leu Arg Asp Met Asn Asn Lys Asp Ala Arg Gln Lys Ile Lys
145                 150                 155                 160

Asp Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
```

```
            180                 185                 190

Phe Leu Lys His Pro Asn Gly Asp Lys Ser Leu Ser Thr Leu His Arg
        195                 200                 205

Leu Asn Ala Tyr Asp Gln Asn Gly Gly Leu Val Ala Lys Leu Val Ala
    210                 215                 220

Thr Asp Asp Arg Thr Val Glu Asp Glu Lys Asp Gly His Arg Ile Leu
225                 230                 235                 240

Asn Ser Leu Phe Glu Arg Phe Asp Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 22
<211> LENGTH: 281
<212> TYPE: PRT
<213> ORGANISM: Influenza B virus

<400> SEQUENCE: 22

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Leu Ser Trp Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
     50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Met Lys Ser Ser Ser Asn Ser Asn
            100                 105                 110

Tyr Pro Lys Tyr Asn Trp Thr Asp Tyr Pro Ser Thr Pro Gly Arg Cys
        115                 120                 125

Leu Asp Asp Ile Glu Glu Glu Thr Glu Asp Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270
```

```
Arg Leu Ser Pro Glu Glu Gly Asp Asn
        275                 280


<210> SEQ ID NO 23
<211> LENGTH: 281
<212> TYPE: PRT
<213> ORGANISM: Influenza B virus

<400> SEQUENCE: 23

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30

Arg Leu Ser Trp Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
     50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Met Lys Ser Ser Ser Asn Ser Asn
            100                 105                 110

Tyr Pro Lys Tyr Asn Trp Thr Asn Tyr Pro Ser Thr Pro Gly Arg Cys
        115                 120                 125

Leu Asp Asp Ile Glu Glu Glu Thr Glu Asp Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Pro Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 24
<211> LENGTH: 281
<212> TYPE: PRT
<213> ORGANISM: Influenza B virus

<400> SEQUENCE: 24

Met Ala Asp Asn Met Thr Thr Thr Gln Ile Glu Val Gly Pro Gly Ala
  1               5                  10                  15

Thr Asn Ala Thr Ile Asn Phe Glu Ala Gly Ile Leu Glu Cys Tyr Glu
             20                  25                  30
```

-continued

```
Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asp Pro Ser Ala Gly
                85                  90                  95

Ile Glu Gly Phe Glu Pro Tyr Cys Met Lys Ser Ser Ser Asn Ser Asn
            100                 105                 110

Cys Pro Lys Tyr Asn Trp Thr Asp Tyr Pro Ser Thr Pro Gly Arg Cys
        115                 120                 125

Leu Asp Asp Ile Glu Glu Glu Pro Glu Asp Val Asp Gly Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 25
<211> LENGTH: 281
<212> TYPE: PRT
<213> ORGANISM: Influenza B virus

<400> SEQUENCE: 25

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asp Pro Ser Ala Gly
                85                  90                  95

Ile Glu Gly Phe Glu Pro Tyr Cys Met Lys Ser Ser Ser Asn Ser Asn
            100                 105                 110

Cys Pro Lys Tyr Asn Trp Thr Asp Tyr Pro Ser Thr Pro Gly Arg Cys
        115                 120                 125
```

-continued

```
Leu Asp Asp Ile Glu Glu Glu Pro Glu Asp Val Asp Gly Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Met Gly Val Leu Ser Gln Phe Gly Gln Glu His
            260                 265                 270

Arg Leu Ser Pro Glu Glu Gly Asp Asn
        275                 280
```

COMPOSITIONS AND VACCINES AGAINST INFLUENZA A AND INFLUENZA B INFECTIONS

CROSS REFERENCE TO RELATED APPLICATIONS

This application claims the benefit of U.S. provisional application Ser. No. 60/737,742 filed on Nov. 18, 2005. The teachings of that application are incorporated herein to the extent they are not inconsistent with the instant disclosure.

STATEMENT REGARDING FEDERALLY FUNDED RESEARCH

The Research leading to the present invention was supported in part, by National Institutes of Health Grants No. P50-GM62413 (to G. T. Montelione) and R01-AI11772 (to R. M. Krug). Accordingly, the U.S. Government may have certain rights in this invention.

FIELD OF THE INVENTION

The present invention relates to useful vaccines for prophylaxis and treatment of influenza A and influenza B viral infections based on the identification of specific amino acid residues in the influenza virus non-structural protein 1 (NS1) involved in protein-RNA interactions which are essential for viral virulence, also disclosed herein.

BACKGROUND

Influenza virus is a major human health problem. It causes a highly contagious acute respiratory illness known as influenza. The 1918-1919 pandemic of the "Spanish influenza" was estimated to cause about 500 million cases resulting in 20 million deaths worldwide (Robbins, 1986). The genetic determinants of the virulence of the 1918 virus have still not been identified, nor have the specific clinical preventatives or treatments that would be effective against such a re-emergence. See, Tumpey, et al., PNAS USA 99(15):13849-54 (2002).

Typical influenza epidemics cause increases in incidence of pneumonia and lower respiratory disease as witnessed by increased rates of hospitalization or mortality. The elderly or those with underlying chronic diseases are most likely to experience such complications, but young infants also may suffer severe disease.

Not surprisingly, there is significant concern of the potential impact of a re-emergent 1918 or 1918-like influenza virus, whether via natural causes or as a result of bioterrorism. Even in nonpandemic years, influenza virus infection causes some 20,000-40,000 deaths per year in the United States alone (Wright & Webster, (2001) Orthomyxoviruses. In "Fields Virology, 4th Edition" (D. M. Knipe, and P. M. Howley, Eds.) pp. 1533-1579. Lippincott Williams & Wilkins, Philadelphia, Pa.). In addition, there are countless losses both in productivity and quality of life for people who overcome mild cases of the disease in just a few days or weeks. Another complicating factor is that influenza A virus undergoes continual antigenic change resulting in the emergence of new strains each year.

Thus, there is a continuing need for new classes of influenza virus vaccines.

SUMMARY OF INVENTION

The instant invention addresses this and other long felt needs by providing in one aspect an attenuated influenza A virus vaccine comprising eight viral RNA segments, wherein a viral RNA segment eight has a first mutation which causes a substitution of a first amino acid corresponding to an amino acid of SEQ. ID. NO. 1 at a position 5, 31, 34, 35, 38, 41, 45, 46, or 49; and wherein said first mutation decreases the dsRNA binding ability of the NS1A protein. The attenuated influenza A virus vaccine may further comprise at least a second mutation, wherein at least the second mutation causes a substitution of at least the second amino acid of SEQ. ID. NO. 1, and wherein the position of the first amino acid is different from the position of at least the second amino acid. In this aspect of the invention the attenuated influenza virus vaccine contains at least the second mutation which causes a substitution of at least a second amino acid corresponding to an amino acid of SEQ. ID. NO. 1 at a position 5, 31, 34, 35, 38, 41, 45, 46, or 49. Further, in one embodiment, the vaccine according to the instant aspect of the invention is cold-adapted. In different embodiments, the influenza A virus is selected from the group consisting of a human influenza A virus, a bovine influenza A virus, an equine influenza A virus, a porcine influenza A virus, an avian influenza A virus. In a specific embodiment, the influenza A virus is an avian H5N1 viral strain.

Another aspect of the present invention provides an attenuated influenza B virus vaccine comprising eight viral RNA segments, wherein a viral RNA segment eight has a first mutation which causes a substitution of a first amino acid corresponding to an amino acid of SEQ. ID. NO. 2 at a position 17, 43, 46, 47, 50, 53, 57, 58, or 61; and wherein said first mutation decreases the dsRNA binding ability of the NS1B protein. In one embodiment, the attenuated influenza B virus vaccine may further comprise at least a second mutation. In one embodiment of the instant invention, the first amino acid and at least the second amino acid correspond to amino acids of SEQ. ID. NO. 2 at different positions. In one embodiment, at least the second mutation causes a substitution of at least a second amino acid corresponding to an amino acid of SEQ. ID. NO. 2 at a position 17, 43, 46, 47, 50, 53, 57, 58, or 61. Further, the influenza B virus may be a cold-adapted influenza B virus. The attenuated influenza B virus vaccine is a human influenza B virus.

In another aspect, the invention provides a pharmaceutical composition comprising the attenuated influenza virus A vaccine or the influenza B vaccine according to the previous aspects of the invention and a pharmaceutically acceptable carrier or diluent.

In yet another aspect, the invention provides a method of prophylaxis of a disease condition caused by the influenza A or influenza B virus comprising administering to a subject in need thereof a therapeutically effective amount of the attenuated influenza virus vaccine according to the previous aspect of the invention.

BRIEF DESCRIPTION OF THE FIGURES

FIG. 1 is an illustration of a model of interaction between the dsRNA binding domain of the NS1A protein and either a major groove of a dsRNA (FIG. 1B) or a minor groove of the dsRNA (FIG. 1C). This binding mode, discovered by the inventors of this patent and first disclosed in U.S. provisional application Ser. No. 60/737,742 filed on Nov. 18, 2005, differs in critical ways from a different binding mode described by Chien et al., 2004 and PCT/US2003/036292 (FIG. 1A), which is incorporated herein in its entirety. The teachings of that PCT/US2003/036292 patent application are incorporated herein to the extent they are not inconsistent with the instant disclosure. The details of the new binding mode(s)

illustrated in FIG. 1 provide critical information on the surface epitope of NS1A involved in dsRNA recognition and binding, upon which this invention is based.

FIG. 2 is an illustration of a model of interaction between the dsRNA binding domain of the NS1B protein and either a major groove of a dsRNA (FIG. 2B) or a minor groove of the dsRNA (FIG. 2C). This binding mode, discovered by the inventors of this patent and first disclosed in U.S. provisional application Ser. No. 60/737,742 filed on Nov. 18, 2005, differs in critical ways from a different binding mode described by Chien et al., 2004 and PCT/US2003/036292 (FIG. 2A), which is incorporated herein in its entirety. The teachings of that PCT/US2003/036292 patent application are incorporated herein to the extent they are not inconsistent with the instant disclosure. The details of the new binding mode(s) illustrated in FIG. 1 provides critical information on the surface epitope of NS1B involved in dsRNA recognition and binding, upon which this invention is based.

DETAILED DESCRIPTION OF PREFERRED EMBODIMENTS

The invention relates to attenuated influenza A and B virus vaccines comprising eight viral RNA segments, wherein viral RNA segment eight has a mutation which decreases the dsRNA binding ability of the NS1A and NS1B proteins.

For a better understanding of the invention, the following non-limiting definitions are provided:

A person of ordinary skill in the art will appreciate that changing more than one (1) base in a codon of interest will significantly reduce the risk that the genetically engineered attenuated influenza A or B virus will back mutate to wild type. Accordingly, "first mutation" and "at least the second mutation" each refer to altering at least 1 or preferably more bases in the same codon.

The phrase "corresponding to an amino acid in position X" of the NS1A or NS1B proteins or dsRNA binding domains thereof, refers to being aligned with the corresponding amino acid position of SEQ. ID. NO. 1 (for the NS1A protein or the dsRNA binding domain thereof) or SEQ. ID. NO. 2 (for the NS1B protein or the dsRNA binding domain thereof) in the non-limiting examples below.

SEQ. ID. NO. 1 is as follows:

```
 1 MDPNTVSSFQ VDCFLWHVRK RVADQELGDA PFLDRLRRDQ KSLRGRGSTL GLDIETATRA
61 GKQIVERILK EES
```

SEQ. ID. NO. 2 is as follows:

```
 1 MADNMTTTQI EVGPGATNAT INFEAGILEC YERFSWQRAL DYPGQDRLHR LKRKLESRIK
61 THNKSEPENK RMSLEERKAI GVKMMKVLLF MDPSAGIEGF EPY
```

In addition, the following amino acid sequences of the NS1 protein of various strains of influenza A virus are set forth below.

The amino acid sequence of the NS1 protein of Influenza A virus, A/Udorn/72 (SEQ. ID. NO. 3):

```
  1 MDPNTVSSFQ VDCFLWHVRK RVADQELGDA PFLDRLRRDQ KSLRGRGSTL GLDIETATRA
 61 GKQIVERILK EESDEALKMT MASVPASRYL TDMTLEEMSR EWSMLIPKQK VAGPLCIRMD
121 QAIMDKNIIL KANFSVIFDR LETLILLRAF TEEGAIVGEI SPLPSLPGHT AEDVKNAVGV
181 LIGGLEWNDN TVRVSETLQR FAWRSSNENG RPPLTPKQKR EMAGTIRSEV
```

The amino acid sequence of the NS1 protein of Influenza A virus, A/goose/Guangdong/3/1997(H5N1) (SEQ. ID. NO. 4):

```
  1 MDSNTITSFQ VDCYLWHIRK LLSMSDMCDA PFDDRLRRDQ KALKGRGSTL GLDLRVATME
 61 GKKIVEDILK SETNENLKIA IASSPAPRYV TDMSIEEMSR EWYMLMPRQK ITGGLMVKMD
121 QAIMDKRIIL KANFSVLFDQ LETLVSLRAF TESGAIVAEI SPIPSVPGHS TEDVKNAIGI
181 LIGGLEWNDN SIRASENIQR FAWGIRDENG GPSLPPKQKR YMAKRVESEV
```

The amino acid sequence of the NS1 protein of Influenza A VIRUS A/QUAIL/NANCHANG/12-340/2000 (H1N1) (SEQ. ID. NO. 5):

```
  1 ELGDAPFLDR LRRDQKSLKG RGSTLGLNIE TATCVGKQIV ERILKEESDE AFKMTMASAL
 61 ASRYLTDMTI EEMSRDWFML MPKQKVAGPL CVRMDQAIMD KNIILKANFS VIFDRLETLT
121 LLRAFTEEGA IVGEISPLPS LPGHTNEDVK NAIGVLIGGL EWNDNTVRVS ETL
```

The amino acid sequence of the NS1 protein of Influenza A virusgi|577477|gb|AAA56812.1|[577477] (SEQ. ID. NO. 6):

```
  1 MDSNTVSSFQ VDCFLWHVRK RFADQEMGDA PFLDRLRRDQ KSLGGRGSTL GLDIETATRA
 61 GKQIVEPILE EESDEALKMT IASAPVSRYL PDMTLEEMSR DWFMLMPKQK VAGSLCIRMD
121 QAIMDKNITL KANFSIIFDR LETLILLRAF TEEGAIVGEI SPVPSLPGHT DEDVKNAIGV
181 LIGGLEWNDN TVRDSETLQR FAWRSSNEDR RPPLPPKQKR KMARTIESEV
```

The amino acid sequence of the NS1 protein of Influenza A virusgi|1413859|gb|AAA43491.1|[413859] (SEQ. ID. NO. 7):

```
  1 MDSNTVSSFQ VDCFLWHVRK RFADQERGDA PFLDRLRRDQ KSLRGRGSTL GLDIETATCA
 61 GKQIVERILK EESDEALKMT IASVPASRYL TDMTLEEMSR DWFMLMPKQK VAGSLCIRMD
121 QAIMDKNIIL KANFSVIFDR LETLILLRAF TEEGAIVGEI SPLPSLPGHT DEDVKNAIGV
181 LIGGLEWNDN TVRVSETLQR FAWRSSNEDG RPPFPPKQKR KMARTIESEV
```

The amino acid sequence of the NS1 protein of Influenza A virusgi|3250851|gb|AAA43684.1|[325085] (SEQ. ID. NO. 8):

```
  1 MDSNTVSSFQ VDCFLWHVRK RFADQKLGDA PFLDRLRRDQ KSLRGRASTL GLDIETATRA
 61 GKQIVERILE EESNEALKMT IASVPASRYL TDMTLEEMSR DWFMLMPKQK VAGSLCIRMD
121 QAIMEKSIIL KANFSVIFDR LETLILLRAF TEEGAIVGEI SPLHSLPGHT DEDVKNAVGV
181 LIGGLEWNGN TVRVSENLQR FAWRSRNENE RPSLPPKQKR EVAGTIRSEV
```

The amino acid sequence of the NS1 protein of Influenza A virusgi|324876|gb|AnA43572.1|[324876] (SEQ. ID. NO. 9):

```
  1 NTVSSFQVDC FLWHVRKRFA DQELGDAPFL DRLRRDQKSL RGRGSTLGLD IETATRAGKQ
 61 IVERILVEES DEALKMTIVS MPASRYLTDM TLEEMSRDWF MLMPKQKVAG SLCIRMDQAI
121 MDKNIILKAN FSVISDRLET LILLRAFTEE GAIVGEISPL PSLPGHTDED VKNAIGDLIG
181 GLEWNDNTVR VSETLQRFAW RSSNEDGRPL LPPKQKRKMA RTIESEV
```

The amino acid sequence of the NS1 protein of Influenza A virusgi|324862|gb|AnA43553.1 [324862] (SEQ. ID. NO. 10):

```
  1 MDPNTVSSFQ VDCFLWHVRK QVADQELGDA PFLDRLRRDQ KSLRGRGSTL GLNIETATRV
 61 GKQIVERILK EESDEALKMT MASAPASRYL TDMTIEEMSR DWFMLMPKQK VAGPLCIRMD
121 QAIMDKNIIL KANFSVIFDR LETLILLRAF TEAGAIVGEI SPLPSLPGHT NEDVKNAIGV
181 LIGGLEWNDN TVRVSKTLQR FAWRSSDENG RPPLTPK
```

The amino acid sequence of the NS1 protein of Influenza A virusgi|324855|gb|AAA43548.1|[324855] (SEQ. ID. NO. 11):

1 NTVSSFQVDC FLWHVLKRFA DQELGDAPFL DRLRRDQKSL RGRGSTLGLD IETATRAGKQ

61 IVERILEEES DEALKMNIAS VPASRYLTDM TLEEMSRDWF MLMPKQKVAG SLCIRMDQAI

121 MDKNIILKAN FSVIFDRLET LILLRAFTEE GAIVGEISPL PSLPGHTDED VKNAIGILIG

181 GLEWNDNTVR VSETLQRFAW RSSNEDGRPP LPPKQKWKMA RTIEPEV

The amino acid sequence of the NS1 protein of Influenza A virusgi|1324778|gb|AAA43504.1|[324778] (SEQ. ID. NO. 12):

1 NTVSSFQVDC FLWHVRKRFA DLELGDAPFL DRLCRDQKSL RGRSSTLGLD IETATRAGKQ

61 IVERILEEES DETLKMTIAS APAFRYPTDM TLEEMSRDWF MLMPKQKVAG SLCIRMDQAI

121 MDKNIILKAN FSVIFDRLET LILLRAFTEE GAIVGEISPL PSLPGHTNED VKNAIGDLIG

181 GLEWNDNTVR VSETLQRFAW RSSNEGGRPP LPPKQKRKMA RTIESEV

The amino acid sequence of the NS1 protein of Influenza A virus, A/PR/8/34 (SEQ. ID. NO. 13):

1 MDSNTITSFQ VDCYLWHIRK LLSMRDMCDA PFDDRLRRDQ KALKGRGSTL GLDLRVATME

61 GKKIVEDILK SETDENLKIA IASSPAPRYI TDMSIEEISR EWYMLMPRQK ITGGLMVKMD

121 QAIMDKRITL KANFSVLFDQ LETLVSLRAF TDDGAIVAEI SPIPSMPGHS TEDVKNAIGI

181 LIGGLEWNDN SIRASENIQR FAWGIRDENG GPPLPPKQKR YMARRVESEV

The amino acid sequence of the NS1 protein of Influenza A virus, A/turkey/Oregon/71 (H7N5) (SEQ. ID. NO. 14):

1 MDSNTITSFQ VDCYLWHIRK LLSMRDMCDA PFDDRLRRDQ KALKGRGSTL GLDLRVATME

61 GKKIVEDILK SETDENLKIA IASSPAPRYI TDMSIEEISR EWYMLMPRQK ITGGLMVRPL

121 WTRG

The amino acid sequence of the NS1 protein of Influenza A virus, A/Hong Kong/1073/99 (H9N2) (SEQ. ID. NO. 15):

1 MDSNTVSSFQ VDCFLWHVRK RFADQELGDA PFLDRLRRDQ KSLRGRGSTL GLDIRTATRE

61 GKHIVERILE EESDEALKMT IASVPASRYL TEMTLEEMSR DWLMLIPKQK VTGPLCIRMD

121 QAVMGKTIIL KANFSVIFNR LEALILLRAF TDEGAIVGEI SPLPSLPGHT DEDVKNAIGV

181 LIGGLEWNDN TVRVSETLQR FTWRSSDENG RSPLPPKQKR KVERTIEPEV

The amino acid sequence of the NS1 protein of Influenza A virus, A/FortMonmouth/1/47-MA (H1N1) (SEQ. ID. NO. 16):

1 MDPNTVSSFQ VDCFLWHVRK RVADQELGDA PFLDRLRRDQ KSLKGRGSTL GLNIETATRV

61 GKQIVERILK EESDEALKMT MASAPASRYL TDMTIEEMSR DWFMLMPKQK VAGPLCIRMD

121 QAIMDKSIIL KANFSVIFDR LETLILLRAF TEEGAIVGEI SPLPSLPGHT NEDVKNAIGV

181 LIGGLEWNDN TVRVSKTLQR FA

In addition, the following amino acid sequences of the NS1 protein of various influenza B strains are disclosed below.

The amino acid sequence of the NS1 protein of the influenza B virus (B/Lee/40) (SEQ. ID. NO. 17):

```
  1 MADNMTTTQI EVGPGATNAT INFEAGILEC YERFSWQRAL DYPGQDRLHR LKRKLESRIK
 61 THNKSEPENK RMSLEERKAI GVKMMKVLLF MDPSAGIEGF EPYCVKNPST SKCPNYDWTD
121 YPPTPGKYLD DIEEEPENVD HPIEVVLRDM NNKDARQKIK DEVNTQKEGK FRLTIKRDIR
181 NVLSLRVLVN GTFLKHPNGD KSLSTLHRLN AYDQNGGLVA KLVATDDRTV EDEKDGHRIL
241 NSLFERFDEG HSKPIRAAET AVGVLSQFGQ EHRLSPEEGD N
```

The amino acid sequence of the NS1 protein of the influenza B virus B/Memphis/296 (SEQ. ID. NO. 18):

```
  1 MADNMTTTQI EVGPGATNAT INFEAGILEC YERLSWQRAL DYPGQDRLNR LKRKLESRIK
 61 THNKSEPESK RMSLEERKAI GVKMMKVLLF MDPSAGIEGF EPYCMKSSSN SNCPKYNWTD
121 YPSTPGRCLD DIEEEPEDVD GPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERLNEG HSKPIRAAET AVGVLSQFGQ EHRLSPEEGD N
```

The amino acid sequence of the NS1 protein of the influenza B virusgi|3252641|gb|AhA43761.1|[325264] (SEQ. ID. NO. 19):

```
  1 MADNMTTTQI EVGPGATNAT INFEAGILEC YERLSWQRAL DYPGQDRLNR LKRKLESRIK
 61 THNKSEPESK RMSLEERKAI GVKMMKVLLF MNPSAGIEGF EPYCMKNSSN SNCPNCNWTD
121 YPPTSGKCLD DIEEEPENVD DPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERFNEG HSKPIRAAET AVGVLSQFGQ EHRLSPEEGD N
```

The amino acid sequence of the NS1 protein of the influenza B virus B/Ann Arbor/1/66 [gi|325261|gb|AhA43759.1|[325261]] (SEQ. ID. NO. 20):

```
  1 MADNMTTTQI EVGPGATNAT INFEAGILEC YERLSSQRAL DYPGQDRLNR LKRKLESRIK
 61 THNKSEPESK RMSLEERKAI GVKMMKVLLF MNPSAGIEGF EPYCMKNSSN SNCPNCNWTD
121 YPPTPGKCLD DIEEEPENVD DPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERFNEG HSKPIRAAET AVGVLSQFGQ EHRLSPEEGD N
```

The amino acid sequence of the NS1 protein of the influenza B virus gi|325256|gb|AnA43756.1|[325256] (SEQ. ID. NO. 21):

```
  1 MADNMTTTQI EVGPGATNAT INFEAGILEC YERFSWQRAL DYPGQDRLHR LKRKLESRIK
 61 THNKSEPENK RMSLEERKAI GVKMMKVLLF MDPSAGIEGF EPYCVKNPST SKCPNYDWTD
121 YPPTPGKYLD DIEEEPENVD HPIEVVLRDM NNKDARQKIK DEVNTQKEGK FRLTIKRDIR
181 NVLSLRVLVN GTFLKHPNGD KSLSTLHRLN AYDQNGGLVA KLVATDDRTV EDEKDGHRIL
241 NSLFERFDEG HSKPIRAAET AVGVLSQFGQ EHRLSPEEGD N
```

The amino acid sequence of the NS1 protein of the influenza B virus (B/Shangdong/7/97) (SEQ. ID. NO. 22):

```
1 MADNMTTTQI EVGPGATNAT INFEAGILEC YERLSWQRAL DYPGQDRLNR LKRKLESRIK
61 THNKSEPESK RMSLEERKAI GVKMMKVLLF MDPSAGIEGF EPYCMKSSSN SNYPKYNWTD
121 YPSTPGRCLD DIEEETEDVD DPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERLNEG HSKPIRAAET AVGVLSQFGQ EHRLSPEEGD N
```

The amino acid sequence of the NS1 protein of the influenza B virus (B/Nagoya/20/99) (SEQ. ID. NO. 23):

```
1 MADNMTTTQI EVGPGATNAT INFEAGILEC YERLSWQRAL DYPGQDRLNR LKRKLESRIK
61 THNKSEPESK RMSLEERKAI GVKMMKVLLF MDPSAGIEGF EPYCMKSSSN SNYPKYNWTN
121 YPSTPGRCLD DIEEETEDVD DPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERLNEG HPKPIRAAET AVGVLSQFGQ EHRLSPEEGD N
```

The amino acid sequence of the NS1 protein of the influenza B virus(B/Saga/S172/99) (SEQ. ID. NO. 24):

```
1    MADNMTTTQI EVGPGATNAT INFEAGILEC YERLSWQRAL DYPGQDRLNR LKRKLESRIK
61   THNKSEPESK RMSLEERKAI GVKMMKVLLF MDPSAGIEGF EPYCMKSSSN SNCPKYNWTD
121  YPSTPGRCLD DIEEEPEDVD GPTEIVLRDM NNKDARQKIK EEVNTQKEGK FRLTIKRDIR
181  NVLSLRVLVN GTFLKHPNGY KSLSTLHRLN AYDQSGRLVA KLVATDDLTV EDEEDGHRIL
241. NSLFERLNEG HSKPIRAAET AVGVLSQFGQ EHRLSPEEGD N
```

The amino acid sequence of the NS1 protein of the influenza B virus (B/Kouchi/193/99) (SEQ. ID. NO. 25):

```
1 MADNMTTTQI EVGPGATNAT INFEAGILEC YERLSWQRAL DYPGQDRLNR LKRKLESRIK
61 THNKSEPESK RMSLEERKAI GVKMMKVLLF MDPSAGIEGF EPYCMKSSSN SNCPKYNWTD
121 YPSTPGRCLD DIEEEPEDVD GPTEIVLRDM NNKDARQKIK EEVNTQKEGK FRLTIKRDIR
181 NVLSLRVLVN GTFLKHPNGY KSLSTLHRLN AYDQSGRLVA KLVATDDLTV EDEEDGHRIL
241 NSLFERLNEG HSKPIRAAET AMGVLSQFGQ EHRLSPEEGD N
```

Influenza viruses are the only members of the orthomyxoviridae family, and are classified into three distinct types (A, B, and C), based on antigenic differences between their nucleoprotein (NP) and matrix (M) protein (Pereira, (1969) Progr. Molec. Virol. 11:46). Only influenza A and B viruses cause significant disease in humans. Influenza A viruses have been isolated from humans, mammals and birds, and are classified according to their surface glycoproteins, hemagglutinin (HA) and neuraminidase (NA). In contrast, influenza B viruses are largely, if not totally, confined to humans. Influenza viruses are enveloped viruses of approximately 100 nm in diameter. The influenza virions consist of an internal ribonucleoprotein core (a helical nucleocapsid) containing a single-stranded RNA genome, and an outer lipoprotein envelope lined inside by a matrix protein (M).

The segmented genomes of influenza A and B viruses consist of eight molecules of linear, negative polarity, single-stranded RNAs which encode eleven polypeptides, including: the RNA-directed RNA polymerase proteins (PB2, PB1 and PA) and nucleoprotein (NP) which form the nucleocapsid; the matrix protein (M1): a surface ion channel protein (M2); two major surface glycoproteins which project from the lipoprotein envelope: hemagglutinin (HA) and neuraminidase (NA); the NS2 protein (or NEP) that mediates the nuclear export of viral nucleocapsids; and two nonstructural proteins: PB1-F2, which has apoptotic functions; and NS1, whose function is described below.

Transcription and replication of the genome takes place in the nucleus and assembly occurs via budding on the plasma membrane. The viruses can reassort genes during mixed infections. Replication and transcription of influenza virus RNA requires four virus-encoded proteins: the NP and the three components of the viral RNA-dependent RNA polymerase, PB1, PB2 and PA (Huang, et al., 1990, J. Virol. 64: 5669-5673). The NP is the major structural component of the virion, which interacts with genomic RNA, and is required for anti-termination during viral RNA synthesis (Beaton & Krug, 1986, Proc. Natl. Acad. Sci. USA 83:6282-6286), and for elongation of RNA chains during replication of viral RNAs (Shapiro & Krug, 1988, J. Virol. 62: 2285-2290).

The influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed as the essential initial event in infection. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the templateindependent addition of poly(A) tracts.

Of the eight viral mRNA molecules so produced in cells infected by influenza A viruses, five are monocistronic messages that are translated directly into the proteins representing HA, NA, NP and two viral polymerase proteins, PB2 and PA. The PB1 mRNA encodes both the PB1 protein and the small PB1-F2 apoptotic protein The M1 and NS1 mRNAs not only encode the M1 and NS1 protein, respectively, but also undergo inefficient splicing, yielding mRNAs that are translated to produce M2 and NS2 (NEP), respectively. The influenza B virus mRNAS differ in several respects: a PB1-F2 protein has not been detected; the NA mRNA encodes not only NA, but also a small protein called NB; and the M1 mRNA is not spliced, but instead encodes two proteins, M1 and BM2 in two different reading frames.

Eukaryotic cells defend against viral infection by producing a battery of proteins, among them interferons. The NS1 protein facilitates replication and infection of influenza virus by inhibiting interferon production in the host cell. The NS1 proteins of human influenza A viruses are 200-237 amino acids long, whereas the NS1 proteins of avian influenza A viruses are more variable variable in length (Parvin et al., (1983) Virology 128:512-517). The NS1 proteins of influenza B viruses are 287 amino acids in length.

The dsRNA-binding domain of the NS1A protein contains two functional domains, namely a domain that binds double-stranded RNA (dsRNA), and an effector domain. The effector domain is located in the C-terminal domain of the protein. Some of its functions have been well established. Specifically, the effector domain binds and inhibits the function of two cellular proteins that are required for the 3' end processing of cellular pre-mRNAs: the 30 kDa subunit of the cleavage and polyadenylation specificity factor (CPSF) and poly (A)-binding protein II (PABII) (Nemeroff et al., (1998) Molecular Cell 1:991-1000; Chen et al., (1999) EMBO J. 18: 2273-2283). As a consequence, the processing of cellular pre-mRNAs to produce mature mRNAs (including interferon mRNAs) in the cytoplasm is inhibited (Nemeroff et al., (1998) Molecular Cell 1:991-1000; Noah et al., (2003) Virology 307:386-395; Twu et al., (2006) J. Virol. 80:3957-3965).

The dsRNA-binding domain of non-structural protein 1 from influenza A viruses (NS1A) is located at its amino terminal end (Qian et al., 1994). An amino-terminal fragment, which is comprised of the first 73 amino-terminal amino acids [NS1A(1-73)], possesses all the dsRNA-binding properties of the full-length protein (Qian et al, (1995) RNA 1:948-956). NMR solution and X-ray crystal structures of NS1A(1-73) have shown that in solution it forms a symmetric homodimer with a unique six helical chain fold (Chien et al., (1997) Nature Struct. Biol. 4:891-895; Liu et al., (1997) Nature Struct. Biol. 4:896-899).

Each polypeptide chain of the NS1A(1-73) domain consists of three alpha-helices corresponding to the segments Asn4-Asp24 (helix 1), Pro30-Leu50 (helix 2), and Ile54-Lys69 (helix 3). Analysis of NS1A(1-73) surface features based on the 3D structure (Chien, 1997; Liu 1997) suggested two possible nucleic acid binding sites, one involving the solvent exposed stretches of helices 2 and 2' comprised largely of the basic side chains, and the other at the opposite side of the molecule that includes some lysine residues of helices 3 and 3' (Chien et al., 1997; Liu 1997). Subsequent site-directed mutagenesis experiments indicated that the side chains of two basic amino acids (Arg38 and Lys41) in the second alpha-helix are the only amino acid side chains that are required for the dsRNA binding activity of the intact dimeric protein (Wang et al., 1999 RNA 5:195-205). These studies also demonstrated that dimerization of the NS1A(1-73) domain is required for dsRNA binding. The role of the dsRNA-binding activity of the NS1A protein during infection has recently been established by using a recombinant influenza A/Udorn/72 virus expressing a NS1A protein containing a RNA-binding domain in which R38 was mutated to A (Min and Krug (2006). Proceedings National Academy of Sciences 103: 7100-7105). This R38A mutant virus is highly attenuated, and the mutant NS1A protein, like the wt protein, is localized in the nucleus. Using the R38A mutant virus, it was established that dsRNA binding by the NS1A protein does not inhibit production of interferon-beta mRNA. Rather, the only significant role of this dsRNA binding activity is to protect the virus against the antiviral state induced by interferon-beta. The enhanced sensitivity of the mutant virus to interferon-beta-induced antiviral activity is due predominantly to the activation of RNase L. Because activation of RNase L is totally dependent on dsRNA activation of 2'-5' oligo (A) synthetase (OAS), these results indicate that the primary role of dsRNA-binding by the NS1A protein in virus-infected cells is to sequester dsRNA away from 2'-5' OAS.

The N-terminal structural domain of the NS1B protein includes the first 103 amino acids [NS1B(1-103)]. Its 3D structure has been determined by X-ray crystallography. This analysis provided a 3D structure for the first 93 amino acids, which is a head-to-tail symmetric homodimer that forms a six-helical chain fold similar to that of NS1A(1-73) (Khan, Yin, Montelione & Tong, Protein Data Bank ID 1XEQ). Each polypeptide chain of the NS 1B(1-93) domain dimer consists of three alpha-helices, corresponding to the segments Ala16-Trp36 (helix 1), Tyr42-Asn63 (helix 2), and Leu74-Leu88 (helix 3). This structure of the dsRNA-binding domain of NS1B was not obvious from the 3D structures of NS1A(1-73), since an attempt to model the NS1B RNA-binding domain from the NS 1 A(1-73) structure using state-of-the-art methods had provided an incorrect homology model (Wang et al., 1999). The role of the dsRNA-binding activity of the NS1B protein during infection has not been established.

Circular dichroism and nuclear magnetic resonance (NMR) data reveal that the conformations of both NS1A(1-73) and dsRNA in the complex are similar to their free forms, demonstrating that there is little or no structural change of the protein or dsRNA upon complex formation (Chien et al., 2004). NMR chemical shift perturbation experiments, which identify atoms for which NMR resonance frequencies change upon ligand binding, show that the dsRNA-binding epitope of NS1A(1-73) is associated primarily with helices 2 and 2'(Chien et al., 2004). Analytical gel filtration and gel shift studies of the interaction between NS1A(1-73) and different double-stranded nucleic acids indicate that NS1A(1-73) recognizes canonical A-form dsRNA, but does not bind to dsDNA or dsRNA-DNA hybrids, which feature B-type and A/B-type intermediate conformations, respectively (Chien et al., 2004).

The crystal structure of NS1B(1-103), together with an analysis of common features between the structure of NS1A (1-73) and NS1B(1-103) provide a working model of the complexes between (i) NS1A(1-73) and dsRNA (FIG. 1) and (ii) between NS1B(1-103) and dsRNA (FIG. 2). Although the available data do not distinguish binding modes in which the major or minor groove, respectively, of dsRNA are at the protein-dsRNA interface, in either of these binding modes the dsRNA-binding epitope on the surface of NS1A or NS1B, respectively, is the same and is unambiguously defined. These experimentally-based models of NS1A-dsRNA and NS1B-dsRNA complexes provide a common basis for the current invention, a novel process for inhibiting influenza infection and for construction of mutant influenza A and B viruses suitable for the development of attenuated virus vaccines.

The newly characterized models of the complex between dsRNA and RNA binding domains of NS1A and NS1B are consistent with published site-directed mutagenesis studies (Wang et al., 1999), demonstrating that the basic side chains of four residues on the surface of NS1A(1-73) are required for dsRNA binding, residues Arg38, Arg38', Lys41, and Lys41' (Wang et al., 1999). Mutation of these residues to alanine results in a dimeric NS1(1-73) molecule which has no detectable dsRNA-binding activity, based on gel shift assays. Utilizing the recently developed reverse genetic system, whereby influenza viruses can be generated by transfection of multiple DNAs without a helper virus (Fodor et al., 1999; Neumann et al., 1999), a recombinant influenza A virus encoding a NS1A protein containing a substitution of arginine for alanine at position 38 (R38A) domain was generated. This virus is highly attenuated; it forms pin-point plaques and the rate of virus replication and virus yield after low multiplicity of infection (0.001 plaque-forming units/cell) is approximately 1000-fold lower than with wild-type virus. In contrast to others (Donelan et al, 2003), the analysis of the defects of this virus mutant demonstrate that the primary, if not the only, function of the NS1A RNA-binding domain is to block the activation of the interferon-induced 2'5'-oligo(A) synthetase (Min and Krug (2006). Proceedings National Academy of Sciences 103: 7100-7105). The inability of the mutant virus to block the activation of this enzyme renders the virus extremely sensitive to interferon, an important antiviral protein drug. These data demonstrate that the interaction between NS1A and its RNA targets involving the specific surface binding epitope including residues Arg38, and Arg38' are essential for the viability of the the influenza A viruses, including avian H5N1 viruses.

Thus, in one aspect, the invention provides an attenuated influenza virus comprising eight viral RNA segments, wherein a viral RNA segment eight has a first mutation in a region encoding a dsRNA binding domain of the NS1A protein (SEQ. ID. NO. 1); and wherein said first mutation decreases the dsRNA binding ability of the NS1A protein.

In one embodiment, the amino acid sequence of the instant invention has at least one mutation, compared with natural amino acid sequences of the dsRNA binding domain of the NS1A protein, and therefore exhibits reduced affinity for dsRNA thus attenuating the pathogenic properties a protein which includes the amino acid sequence of the instant invention. As discussed above, the inventors discovered that amino acids in positions 5, 31, 34, 35, 38, 41, 45, 46, and 49 of A/Udorn/72 (a dsRNA binding domain of which is shown in SEQ. ID NO. 1) comprise the dsRNA-binding epitope of NS1A (i.e. the set of surface atoms involved in dsRNA binding), and are critical for the dsRNA binding properties of the NS1A protein. Further, the inventors found that amino acids in positions 38 and 41 are crucial for the dsRNA binding properties of NS1A, and that the Arg in position 38 is critical for determining the virulence of influenza A viruses in cell based assays.

Accordingly, in different embodiments of the invention, influenza A viruses are genetically engineered to have one or more mutations altering the amino acid sequence relative to naturally occurring viruses. Based on circular dichroism spectroscopy, X-ray crystallography, and NMR spectroscopy analyses, the inventors discovered a model of interaction between the dsRNA binding domain of the NS1A protein and a dsRNA, as shown in FIG. 1. This model teaches that amino acids corresponding to amino acids of SEQ. ID. NO. 1 in positions 5, 31, 34, 35, 38, 41, 45, 46, and 49 are important for the proper binding of the dsRNA to the dsRNA binding domain of the NS1A protein. This dsRNA binding epitope is different from the previously identified dsRNA-binding epitope published by Chien et al., 2004. Accordingly, in one embodiment, at least one mutation causes a substitution of a first amino acid corresponding to an amino acid of SEQ. ID. NO. 1 in a position 5, 31, 34, 35, 38, 41, 45, 46, or 49. In another embodiment, the recombinant influenza A virus comprises at least a second mutation which causes a substitution of at least a second amino acid of the NS1A protein. A person of ordinary skill in the art will appreciate that it is preferred that the positions of the first amino acid and the at least second amino acid should be different. For example, the at least second mutation may be in a different portion of the NS1A protein. In another embodiment, the at least second amino acid is also located within the dsRNA-binding domain of the NS1A protein. In a more specific embodiment, at least the second amino acid corresponds to an amino acid of SEQ. ID. NO. 1 in a position 5, 31, 34, 35, 38, 41, 45, 46, or 49. The non-limiting examples of the first and at least the second amino acids include T5A, T5D, R38A, R38D, K41A, K41D, G45D, R46A, T49A, T49D, and any combinations thereof. Further, in different embodiments, the NS1A protein may be selected from the group consisting of a human NS1A protein, a bovine NS1A protein, an equine NS1A protein, a porcine NS1A protein and an avian NS1A protein. In related embodiments of the invention, the influenza virus is an avian H5N1 viral strain.

The inventors have verified the predicted effects of some of these specific mutations in the dsRNA-bindng affinity of NS1A [NS1A(1-73)], including mutations T5A, T5D, G45D, T49A, and T49D. dsRNA-binding affinity was assessed in vitro by dsRNA gel-shift assay, as described in Chien et al, 2004. The T5A variant of NS1A has similar dsRNA affinity compared with the wild-type NS1A. In comparison, significant disruption of dsRNA binding is observed in the T5D mutant of NS1A(1-73). The mutation G45D introduced the most severe disruption of dsRNA among these 5 mutants. Intermediate, but significant, reduction in dsRNA-binding affinity is also observed for both T49A and T49D variants; the change into an aspartic acid at this position, like residue no. 5, results in more severe disruption of complex formation that the alanine mutation. Based on these results, we have validated that residue sites 5, 45, and 49 each play significant roles in determining protein-dsRNA affinities, supporting the models of the dsRNA-NS1A complexes shown in FIG. 1. The widely different dsRNA affinities observed across this set of mutations demonstrates the potential to tune the dsRNA affinity and hence virulence of influenza A viruses, providing a route to producing a culturable live attenuated influenza virus vaccine.

In another aspect, the invention provides influenza B viruses are genetically engineered to have one or more mutations altering the amino acid sequence relative to naturally occurring viruses that include. As discussed above, the inventors discovered that amino acids in positions 17, 43, 46, 47, 50, 53, 57, 58, or 61 of influenza B virus (B/Lee/40) a dsRNA binding domain of which is shown in SEQ. ID NO. 2, are important for the dsRNA binding properties of the NS1B protein. Based on circular dichroism spectroscopy, X-ray crystallography and NMR spectroscopy analyses, the inventors discovered a model of interaction between the dsRNA binding domain of the NS1A protein and a dsRNA, as shown in FIG. 2. This model teaches that amino acids corresponding to amino acids of SEQ. ID. NO. 2 in positions 17, 43, 46, 47, 50, 53, 57, 58, and 61 are important for the proper binding of the dsRNA to the dsRNA binding domain of the NS1A protein. Accordingly, in one embodiment, at least one mutation causes a substitution of a first amino acid corresponding to an amino acid of SEQ. ID. NO. 2 in a position 17, 43, 46, 47, 50, 53, 57, 58, or 61. In another embodiment, the recombinant influenza B virus comprises at least a second mutation which causes a substitution of at least a second amino acid of the NS1B protein. A person of the ordinary skill in the art will appreciate that it is preferred that the positions of the first amino acid and the at least second amino acid should be different. For example, the at least second mutation may be in a different portion of the NS1B protein. In another embodiment, the at least second amino acid is also located within the dsRNA-binding domain of the NS1B protein. In a more specific embodiment, the at least second amino acid corresponds to an amino acid of SEQ. ID. NO. 2 in a position 17, 43, 46, 47, 50, 53, 57, 58, or 61. The non-limiting examples of the first and at least the second amino acids include T17A, T17D, R50A, R50D, R53A, R53D, S57A, S57D, R58A, T61A, T61D, and any combinations thereof. Further, in different embodiments, the NS1B protein may be selected from the group consisting of a human NS1B protein, a bovine NS1B protein, an equine NS1B protein, a porcine NS1B protein and an avian NS1B protein.

A person of ordinary skill in the art will understand that because of the degeneracy of the genetic code, a large number of nucleic acid sequences can be generated in accordance with this invention. Methods for identifying homologous nucleic acid and amino acid sequences are well known in the art and include both hybridization-based and bioinformatics-based approaches (see Baxevanis and Ouellette, *Bioinformatics, A Practical Guide to the Analysis of Genes and Proteins* (2001)).

The production of the viruses of the instant invention (or the respective recombinant NS1A protein or respective NS1B protein comprising said amino acid sequences) can be achieved by recombinant DNA technology. Nucleic acid sequences encoding the amino acid sequences of the instant invention can be produced using methods well known in the art, including, for example, chemical synthesis, PCR and site-directed mutagenesis.

In another aspect, the invention provides recombinant influenza A virus and influenza B virus comprising the amino acid sequences which are at least 70% identical but less than 100% identical either to dsRNA binding domains of NS1A or NS1B. These viruses may be generated, for example, by reverse genetic system, whereby influenza virus can be generated by transfection of multiple DNAs without a helper virus. This technique was described in Fodor et al., 1999. Essentially, in that study the technique involved transfecting into a host cell a combination of plasmids containing cDNAs for the viral RNA segments (including NS1 proteins), proteins of viral RNA dependent polymerase complex (PB1, PB2, and PA), and nucleoprotein. Further, it is possible to transfect host cells (such as, for example 293 cells or Vero cells) with a plasmid encoding a recombinant NS1A protein (for rescuing influenza A viral phenotype) or a recombinant NS1B protein (for rescuing influenza B viral phenotype) containing the appropriate amino acid sequence of the instant invention. The resulting viruses may be used for creation of vaccines, as described below.

In another embodiment, the virus can be propagated in suitable host, such as, for example, chicken eggs, without a need for transforming a host cell with multiple plasmids. In this embodiment, essentially, clinical isolates of human influenza virus are taken from infected patients and are reassorted in embryonated chicken eggs with laboratory-adapted master strains of high-growth donor viruses.

To prepare the recombinant NS1A and NS1B viruses for different purposes (including, without limitations, the use of the virus as a vaccine or a part thereof), each of these mutations may be carried out individually on constructs of NS1A and NS1B suitable for biochemical characterization, possibly including but not limited to N-terminal hexahisitidine tagged NS 1A(1-73), C-terminal hexahisitidine tagged NS 1A(1-73), N-terminal hexahisitidine tagged NS1B(1-103), C-terminal hexahisitidine tagged NS1B(1-103). Other affinity tags (e.g. FLAG tags) may also be used. These proteins may be purified and characterized with respect to structural integrity by comparing the circular dichroism and/or NMR spectrum and/or X-ray crystal structures with those of the corresponding wild-type NS1 construct. The several constructs may then be assayed for dsRNA binding as described elsewhere (Chien et al., 2004), or using other methods of assessing protein-dsRNA binding affinities commonly used for such studies, such as, for example, sedimentation equilibrium, gel electrophoresis, or gel filtration chromatography. These data will be used to assess the effect of single site mutants at these sites revealed by the structural models to be important for dsRNA recognition. Further, sets of double, triple, and quadruple mutants of residues at the interface between NS1A or NS1B and dsRNA may be made in the same constructs, and assayed for structural integrity and dsRNA binding affinity. This experimental design will allow a person of the ordinary skill in the art to identify mutant forms of NS1A(1-73) and NS1B (1-103) with minimal structural disruption but lacking dsRNA binding affinity.

The invention encompasses methods of selecting viruses which have the desired phenotype, i.e., viruses which have low or no dsRNA binding activity, whether obtained from natural variants, spontaneous variants (i.e., variants which evolve during virus propagation), mutagenized natural variants, reassortants and/or genetically engineered viruses. Such viruses can be best screened in differential growth assays that compare growth in host systems which have attenuated and normal immune response to the influenza A and B viruses. Viruses which demonstrate better growth in the hosts having the attenuated response versus the normal response are selected; preferably, viruses which grow to titers at least one log greater in the host systems with the attenuated response as compared to the host system with the normal response are selected.

To this end, growth of virus in cell lines as Vero cells versus MDCK cells can be compared. Techniques which are well known in the art for the propagation of viruses in cell lines can be used. Growth of virus in the cell line with the normal response to the influenza A or B virus versus the cell line with the attenuated response to the influenza A or B virus can be compared.

The screening methods of the invention provide a simple and easy screen to identify mutant viruses with diminish the dsRNA binding activity by the inability of the genetically engineered virus of the instant invention to grow in host systems with the normal response to the influenza A or B virus, as compared to the ability of the genetically engineered virus of the instant invention to grow in grow in host systems with the attenuated response. The screening methods of the invention may also be used to identify mutant viruses with altered, but not abolished dsRNA binding activity by measuring the ability of the genetically engineered virus of the instant invention to grow in such systems as, for example, 10-day old embryonated eggs or MDCK cells and such systems as, for example, 6-to-7-day old embryonated eggs or Vero cells.

In accordance with the present invention, immature embryonated chicken eggs encompass eggs which as a course of nature are up to, but not yet ten-day-old eggs, preferably six- to nine-day-old eggs; and eggs which artificially mimic immature eggs up to, but not yet ten-day-old, as a result of alterations to the growth conditions, e.g., changes in incubation temperatures; treating with drugs; or any other alteration which results in an egg with a retarded development and ability to exhibit a proper response to viral infections, as compared to 10- to 12-day-old eggs.

In one embodiment, the present invention relates to growing naturally occurring and engineered mutant viruses in unconventional substrates, such as immature embryonated eggs which have not yet developed mechanisms of fighting viral infections. Immature embryonated eggs are normally not used to grow virus due to their fragile condition and smaller allantoic volume. The present invention encompasses growing the genetically engineered viruses of the instant invention in embryonated eggs less than 10 days old; preferably growing the viruses in 8-day old embryonated eggs and most preferably, in 6 to 8-day old eggs.

The present invention also encompasses methods of growing and isolating mutated viruses having altered dsRNA binding activity in cells and cell lines which naturally exhibit an attenuated response to viral infections as compared to wild-type cells. In a particular preferred embodiment, the present invention relates to methods of growing the viruses of the instant invention in Vero cells.

The invention provides vaccines for prophylaxis of diseases caused by influenza A or influenza B viruses. The invention encompasses vaccine formulations comprising the attenuated negative strand RNA viruses having an impaired ability to bind the dsRNA, and a suitable excipient. The virus used in the vaccine formulation may be selected from naturally occurring mutants or variants, mutagenized viruses or genetically engineered viruses. Attenuated strains of segmented RNA viruses can also be generated via reassortment techniques, or by using a combination of the reverse genetics approach and reassortment techniques. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Vaccine formulations may include genetically engineered influenza A or B viruses that have at least one mutation in the dsRNA binding domain of the NS1 gene, as described above. When formulated as a live virus vaccine, a range of about $10^2$-$10^9$ plaque forming units (PFU)/ml, or any range or value therein (e.g., $10^3$, $10^4$, $10^5$, $10^6$, $10^7$, or $10^8$) per dose should be used.

Many methods may be used to introduce the vaccine formulations described above, these include but are not limited to intranasal, intratracheal, oral, intradermal, intramuscular, intraperitoneal, intravenous, and subcutaneous routes. It may be preferable to introduce the virus vaccine formulation via the natural route of infection of the pathogen for which the vaccine is designed, or via the natural route of infection of the parental attenuated virus. Where a live influenza virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by influenza viruses may induce a strong secretory immune response, for example in the urogenital system, with concomitant protection against a particular disease causing agent.

A vaccine of the present invention could be administered once. Alternatively, a vaccine of the present invention could be administered twice or three times with an interval of 2 to months between doses. Alternatively, a vaccine of the present invention could be administered as often as needed to an animal, preferably a mammal, and more preferably a human being.

In one embodiment, the vaccine comprises an attenuated virus coding for the amino acid sequences describe in the instant invention (e.g., the amino acid sequence which is at least 70% but less than 100% identical to a dsRNA-binding domain of an NS1A protein of an influenza A virus for vaccination against influenza A virus and the amino acid sequence which is at least 70% but less than 100% identical to a dsRNA-binding domain of an NS1B protein of an influenza B virus for vaccination against influenza B virus) in combination with a pharmaceutically acceptable vehicle.

More specifically, the amino acid sequence coded for by an attenudated influenza A virus vaccine which is at least 70% but less than 100% identical to a dsRNA-binding domain of an NS1A protein of an influenza A virus will have at least one mutation in the dsRNA-binding epitope including, without limitation T5A, T5D, R38A, R38D, K41A, K41D, G45D, R46A, T49A, T49D, and any combinations thereof. The amino acid sequence coded for by an attenudated influenza A virus vaccine which is at least 70% but less than 100% identical to a dsRNA-binding domain of an NS1B protein of an influenza B virus will have at least one mutation id the dsRNA-binding epitope including, without limitation T17A, T17D, R50A, R50D, R53A, R53D, S57A, S57D, R58A, T61A, T61D, and any combinations thereof.

The attenuated influenza A or B viral vaccines of the present invention code for an amino acid sequence which is at least 70% identical but less than 100% identical to a dsRNA-binding domain of the NS1A protein of the influenza A virus, or the dsRNA-binding domain of the NS1B protein of the influenza B virus, respectively. Since the amino acid sequences are modified and as such, they may have a diminished dsRNA binding capabilities, the recombinant viruses will be less pathogenic than the unmodified viruses. Accordingly, a person of the ordinary skill in the art will be able to select a combination of mutations, including, without limitation, those mutations described above, thus reaching an advantageous combination of reducing the undesirable side effect and a robust immune response.

Live vaccines are particularly advantageous because they lead to a prolonged stimulus which can confer substantially long-lasting immunity. When the immune response is protective against subsequent influenza A or influenza B infection, the live vaccine itself may be used in a preventative vaccine against influenza A or influenza B viruses.

In another embodiment, the vaccines of the instant invention comprise cold-adapted strains of influenza A and influenza B viruses. The cold-adapted strains of viruses suitable for the vaccines of the instant inventions are known in the art. For example, a suitable strain for cold-adapted influenza B virus is B/Jilin20/03. Suitable non-limiting example of a cold adapted influenza A strain is a cold-adapted strain derived from A/Ann Arbor(AA)/6/60. Edwards, J. Infect. Dis. 169: 68-76 (1994); Murphy, Infect. Dis. Clin. Pract. 2:174-181 (1993).

In one embodiment, the vaccine comprises a pharmaceutically acceptable vehicle. The suitable vehicles may be both aqueous and non-aqueous. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, immunostimulats, immunosuppressants, wetting agents, emulsifying and suspending agents, or any combination thereof.

Suitable adjuvants include, without limitations, incomplete Freund's adjuvant, aluminum phosphate, aluminum hydroxide, or alum, Stimulon® QS-21 (Aquila Biopharmaceuticals, Inc., Framingham, Mass.), MPL® (3-0-deacylated monophosphoryl lipid A; Corixa, Hamilton, Mont.), and interleukin-12 (Genetics Institute, Cambridge, Mass.).

A person of the ordinary skill in the art has a sufficient expertise to determine the dosage of the vaccines of the instant invention. Such dosage depends on the pathogenicity of the virus included in the vaccine and on the ability of the antigen to elicit an appropriate immune response. In different embodiments of the invention, a virus vaccine composition of the instant invention may comprise from about $10^2$-$10^9$ plaque forming units (PFU)/ml, or any range or value therein (e.g., $10^8$, $10^4$, $10^8$, $10^6$, $10^7$, or $10^8$, where the virus is attenuated. A vaccine composition comprising an inactivated virus can comprise an amount of virus corresponding to about 0.1 to 200 μg of the amino acid sequences of the instant invention per ml, or any range or value therein.

The vaccines of the instant invention can be applied in multiple ways. According to one embodiment of the invention, the intranasal administration is via the mucosal route. The intranasal administration of the vaccine composition can be formulated, for example, in liquid form such as, for example, nose drops, spray, or suitable for inhalation. In other embodiment, the vaccine may be administered as a powder, or a cream, or an emulsion.

In another embodiment, the vaccines of the instant invention are applied by an injection, including, without limitation, intradermal, transdermal, intramuscular, intraperitoneal and intravenous.

According to another embodiment of the invention, the administration is oral and the vaccine may be presented, for example, in the form of a tablet or encased in a gelatin capsule or a microcapsule, which simplifies oral application. The production of these forms of administration is within the general knowledge of a technical expert.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

We claim:

1. An attenuated influenza B virus vaccine comprising eight viral RNA segments, wherein one segment of the RNA segments has a first mutation which causes a substitution of a first amino acid corresponding to an amino acid of SEQ. ID. NO. 2, a dsRNA binding domain of an NS1B protein, at a position 17, 43, 46, 57, or 61; and wherein said first mutation decreases the dsRNA binding ability of the NS1B protein.

2. The attenuated influenza B virus vaccine of claim 1, further comprising at least a second mutation anywhere in the dsRNA binding domain of the NS1 protein.

3. The attenuated influenza B virus vaccine of claim 2, wherein at least the second mutation causes a substitution of at least a second amino acid corresponding to an amino acid of SEQ. ID. NO. 2 at a position 17, 43, 46, 47, 50, 53, 57, 58, or 61.

4. The attenuated influenza B virus vaccine of claim 1, wherein the influenza virus is a human influenza B virus.

5. A method of prophylaxis of a disease condition caused by the influenza virus comprising administering to a subject in need thereof a therapeutically effective amount of the attenuated influenza virus vaccine of claim 1.

6. A pharmaceutical composition comprising the attenuated influenza virus vaccine of claim 1 and a pharmaceutically acceptable carrier or diluent.

7. The attenuated influenza B virus vaccine of claim 1 wherein the influenza virus is a cold-adapted influenza virus.

8. The attenuated influenza B virus vaccine of claim 1, wherein said vaccine is capable of eliciting an immune response.

9. An attenuated influenza A virus vaccine comprising eight viral RNA segments, wherein one segment of the RNA segments (i) encodes a mutant form of SEQ ID NO.: 1, a dsRNA binding domain of an NS1A protein, that is at least 70% identical to SEQ ID NO.: 1 and (ii) has a first mutation which causes a substitution of a first amino acid corresponding to an amino acid of SEQ. ID. NO. 1 position 31, 34, 45, or 49.

10. The attenuated influenza A virus vaccine of claim 9, further comprising at least a second mutation anywhere in the dsRNA binding domain of the NS1A protein.

11. The attenuated influenza virus vaccine of claim 10, wherein the at least second mutation causes a substitution of at least a second amino acid corresponding to an amino acid of SEQ. ID. NO. 1 at a position 5, 31, 34, 35, 38, 41, 45, 46, or 49.

12. The attenuated influenza A virus vaccine of claim 11 wherein the influenza virus is a cold-adapted influenza virus.

13. The attenuated influenza A virus vaccine of claim 11, wherein the influenza virus is selected from the group consisting of a human influenza A virus, a bovine influenza A virus, an equine influenza A virus, a porcine influenza A virus, an avian influenza A virus.

14. The attenuated influenza A virus vaccine of claim 11 wherein the influenza virus is an avian H5N1 viral strain.

15. A pharmaceutical composition comprising the attenuated influenza virus vaccine of claim 9 and a pharmaceutically acceptable carrier or diluent.

16. A method of prophylaxis of a disease condition caused by the influenza virus comprising administering to a subject in need thereof a therapeutically effective amount of the attenuated influenza virus vaccine of claim 9.

* * * * *

UNITED STATES PATENT AND TRADEMARK OFFICE

CERTIFICATE OF CORRECTION

PATENT NO. : 9,119,810 B2
APPLICATION NO. : 12/094114
DATED : September 1, 2015
INVENTOR(S) : Gaetano T. Montelione et al.

It is certified that error appears in the above-identified patent and that said Letters Patent is hereby corrected as shown below:

In the Specification

At Column 1, Line number 15 should read:
This invention was made with government support under Grant Nos. P50-GM62413 and R01-AI11772 awarded by The National Institutes of Health. The government has certain rights in the invention.

Signed and Sealed this
Thirtieth Day of April, 2024

Katherine Kelly Vidal

Katherine Kelly Vidal
*Director of the United States Patent and Trademark Office*